United States Patent
Knopp et al.

(10) Patent No.: US 6,639,081 B1
(45) Date of Patent: Oct. 28, 2003

(54) METHOD FOR PRODUCING 4-CYANO-2-AMINOMETHYLTHIAZOLE

(75) Inventors: Monika Knopp, Ludwigshafen (DE); Stefan Koser, Ludwigshafen (DE); Bernd Schaefer, Dierbach (DE)

(73) Assignee: Abbott GmbH & Ci, KG, Munich (DE)

( * ) Notice: Subject to any disclaimer, the term of this patent is extended or adjusted under 35 U.S.C. 154(b) by 0 days.

(21) Appl. No.: 10/031,703

(22) PCT Filed: Jul. 11, 2000

(86) PCT No.: PCT/EP00/06563

§ 371 (c)(1), (2), (4) Date: Apr. 30, 2002

(87) PCT Pub. No.: WO01/07426

PCT Pub. Date: Feb. 1, 2001

(30) Foreign Application Priority Data

Jul. 23, 1999 (DE) .......................... 199 34 066

(51) Int. Cl.[7] .............................. C07D 277/04
(52) U.S. Cl. ........................ 548/201; 548/202
(58) Field of Search ................. 548/201, 202

(56) References Cited

FOREIGN PATENT DOCUMENTS

WO  WO 2000039124 A1 *  7/2000
WO  WO 0107425 A1 *  2/2001

OTHER PUBLICATIONS

Videnov G. et al, 1996, "Synthesis of naturally occuring, conformationally restricted tripepetide mimetics."; Angewandte Chemie. International EDition, Verlag Chemie. Weinheim, DE, Bd. 35, Nr 13/14, p. 1503–1506.*

* cited by examiner

Primary Examiner—Joseph K. McKane
Assistant Examiner—Rei Tsang Shiao
(74) Attorney, Agent, or Firm—Wood, Phillips, Katz, Clark & Mortimer

(57) ABSTRACT

The invention relates to processes for preparing 2-aminomethyl-4-cyanothiazole and its salts of the formulae Ia and Ib

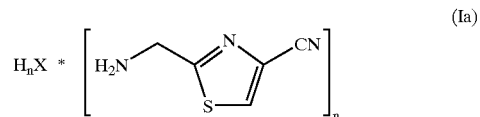

(Ia)

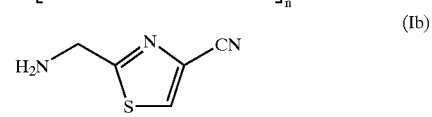

(Ib)

in which
n=1 or 2 and
for n=1, X is chloride, bromide, triflate and hydrogen sulfate and
for n=2, X is sulfate, which comprises the process step where the aminonitrile of the formula II

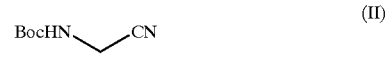

(II)

is stirred with a cysteine ester of the formula III,

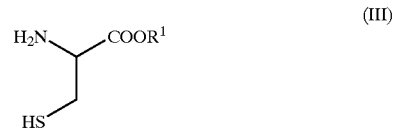

(III)

in which $R^1$ is branched or linear $C_{1-10}$-alkyl or

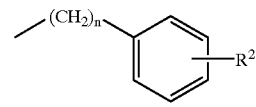

where n=0, 1 or 2 and $R^2$ is branched or linear $C_1$–$C_{10}C_{10}$-alkyl or $C_1$–$C_4$-alkoxy or $C_1$–$C_4$-dialkylamino in an inert solvent in the presence of a base at from 0° C. to 80° C. until the reaction has essentially proceeded to completion, and to the compounds of the formulae Ia and Ib.

16 Claims, No Drawings

METHOD FOR PRODUCING 4-CYANO-2-AMINOMETHYLTHIAZOLE

This application is a 371 of PCT/EP00/06563 Jul. 11, 2000.

Preparation of 4-cyano-2-aminomethylthiazole

The present invention relates to a novel process for preparing 2-aminomethyl-4-cyanothiazole.

Syntheses for preparing 2-aminomethylthiazoles which are substituted in the 4 position by an electron-withdrawing group, such as a carboxylic acid or a carboxylic acid derivative, for example an ester, an amide or a thioamide, have been described in the literature.

The key step of the synthesis sequence is the construction of the thiazole ring. In the customary literature syntheses, the thiazole ring is obtained by reacting a thioamide with a bromopyruvic acid derivative (1) G. Videnov, D. Kaiser, C. Kempter, G. Jung, Angew. Chem. Int. Ed. Engl. 35 (1996), 1503; (2) Y. Nakamura, C. Shin, K. Umemura, J. Yoshimura, Chem. Lett. (1992), 1005; (3) J. A. Sowinski, P. L. Toogwood, J. Org. Chem. 61 (1996), 7671; (4) M. North, G. Pattenden, Tetrahedron 46 (1990), 8267; (5) U. Schmidt, Synthesis 1987, 233; (6) WO 98/6741.

The thioamides used for this purpose are obtained, for example, by reacting an amide with Lawessons' reagent (1), (2), (3), or by reacting an aminonitrile with $H_2S$ (7) K. P. Moder, F. R. Busch, D. C. Richter, Org. Prep. Proced. Int. 24 (1992), 66; G. Li, P. M. Warner, D. J. Jebaratnam, J. Org. Chem. 61 (1961), 778; T. P. Holler, F. Q. Ruan, A. Spaltenstein, P. B. Hopkins, J. Org. Chem. 54 (1989), 4570; T. P . Culbertson, J. M. Dornagala, P. Peterson, S. Bongers, J. B. Nichols, J. Heterocycl. Chem. 24 (1987), 1509; H. Moser, A. Flin, A. Steiger, A. Eschenmesser, Helv. Chim. Acta 69 (1986), 1224.

The processes described in the literature are in most cases only suitable for small batches on a laboratory scale. They employ protective groups which, when used on an industrial scale, would increase preparation costs owing to the high cost of the starting materials. Furthermore, in the case of the synthesis of the thioamides with reaction with $H_2S$, industrial implementation of the process is made difficult owing to high environmental and safety requirements. The synthesis of the thioamides with Lawesson's reagent on an industrial scale is unattractive for economical reasons, owing to the high cost of the starting materials. Furthermore, it has been found that these procedures, when the reaction is conducted on a pilot plant scale, do not give the yields that have been described, and/or can only be realized with very high technical expense.

In addition to the intermolecular cyclizations mentioned, intramolecular cyclizations of an N-(hydroxyethyl) thioamide under Mitsunobo conditions have also been described in the literature (8) C. Shin, A. Ito, K. Okumura, Y. Nakamura, Chem. Left. (1995), 45. However, this method also entails the abovementioned disadvantages.

If it were easily accessible industrially, 2-aminomethyl-4-cyanothiazole would be an interesting intermediate for preparing serine protease inhibiting low-molecular-weight substances (for example thrombin inhibitors). Such thrombin inhibitors are mentioned, for example, in WO 9806741. Moreover, 2-aminomethyl-4-cyanothiazole can be used for preparing other thrombin inhibitors and their prodrugs such as, for example, N-(ethoxycarbonylmethytene)-(D) cyclohexylaianyl-3,4-dehydro-prolyl-[2-(4-hydroxyamidino)thiazole]methylamide hydrochloride.

It is an object of the present invention to provide a process for preparing 2-aminomethyl-4-cyanothiazole, thus making available this synthesis building block cost efficiently for other syntheses.

We have found that this object is achieved by a novel way of constructing the thiazole skeleton which makes the 4-cyano-2-methylthiazole building block industrially accessible.

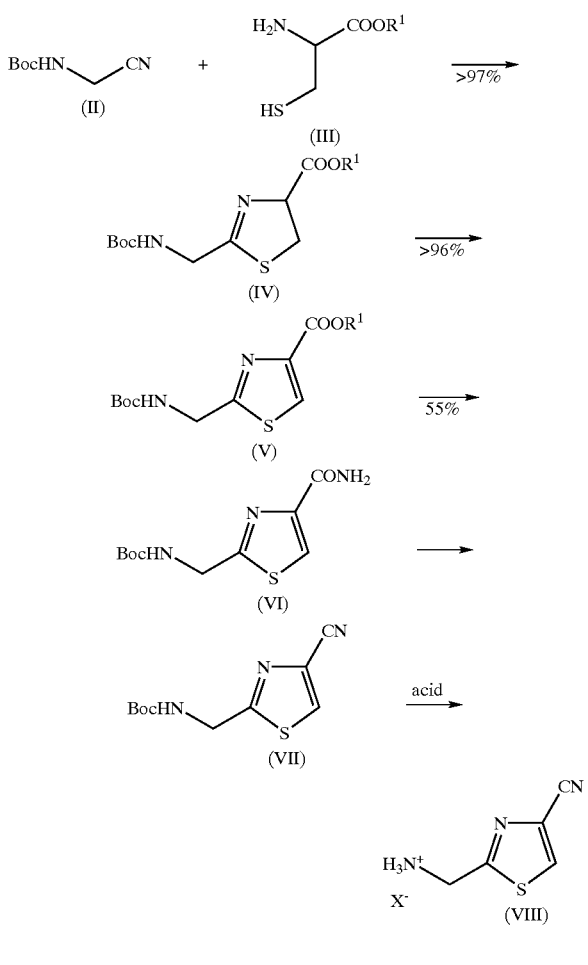

where $R^1$ is branched or straight-chain $C_1$–$C_{10}$-alkyl or

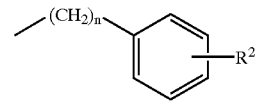

where n=0, 1 or 2 and $R^2$ is branched or straight-chain $C_1$–$C_{10}$-alkyl or $C_1$–$C_4$-alkoxy or $C_1$–$C_4$-dialkylamino. Preferred substituents are —$OCH_3$, $OCH_2CH_3$, $N(CH_3)_2$, $N(C_2H_5)_2$, $CH_3$, $C_2H_5$, $C_3H_7$.

Here, the thiazole ring is obtained by reacting an aminonitrile with L-cysteine, giving the thiazolidine, followed by its oxidative aromatization.

Thiazole syntheses by oxidation of thiazolidines or thiazolanes are known from the literature; however, they have only been described on a laboratory scale. Frequently, these oxidations are carried out using manganese dioxide. However, this variant gives only moderate yields (9) Y. Hamada, K. Kohda, T. Shioiri, Tetrahedron Lett. 25 (1984), 5303. Better yields are obtained by using perbenzoic acid esters in the presence of copper salts (10) F. X. Tavares, A. I. Meyers, Tetrahedron Lett. 35 (1994), 6803; (11) A. I. Meyers, F.X. Tavares, J. Org. Chem. 61 (1996), 8207.

Almost quantitative conversion is obtained in the presence of bromochloroform and DBU (12) D. R. Williams, P. D. Lowder, Y. G. Yu, D. A. Brooks, Tetrahedron Lett. 38 (1997), 331. This reaction is characterized by particularly mild reaction conditions. However, this synthesis, too, has only been carried out on a gram scale.

The preparation of a thiazolidine or thiazolane starting from a cysteine derivative has only rarely been mentioned in the literature. Examples are known where a cysteine ester has been reacted with aminoaldehydes to give the thiazolane (3), (4), which is then converted into the thiazole via the thiazolidine intermediate. However, α-aminoaldehydes are not very stable. Moreover, they are not commercially available, and they therefore have to be prepared from the corresponding amino acids by multi-step processes.

In addition, thiazolidine syntheses are known where the thiazolidine is obtained by reacting the cysteine derivative with imido esters (3), (4), (10), (13) K. Inami, T. Shiba, Bull. Chem. Soc. Jpn. 58 (1985), 352. However, imido esters are likewise not commercially available and have to be synthesized by a multi-step process, for example from an aminonitrile.

According to the invention, the thiazolidine was synthesized from an aminonitrile, with quantitative conversion. The reaction of the cysteine ester hydrochlorides, in particular the methyl and ethyl esters, with the protected aminoacetonitrile is carried out in an inert solvent, for example in cyclic or open-chain ethers, such as THF, dioxane, DME, in acetonitrile, DMF, or chlorinated hydrocarbons such as $CH_2Cl_2$, $CHCl_3$ or in toluene, or in an alcoholic medium ($C_1$–$C_6$-alcohol, preferably isopropanol, ethanol or methanol) in the presence of a base, such as, for example, $NEt_3$, morpholine, pyridine, lutidine, DMAP, DBU, DBN (preferably triethylamine). The thiazolidine can then be oxidized quantitatively to the corresponding thiazole. The oxidation is likewise carried out in inert solvents, such as, for example, chlorinated hydrocarbons, toluene or cyclic and open-chain ethers.

Organic amines, such as $NEt_3$, morpholine, pyridine, DMAP (dimethylaminopyridine) and lutidine serve as base.

In both steps, the crude products can be employed directly in the next step without costly purification.

The next step in the synthesis sequence according to the invention is the aminolysis of the ester to give the amide. The aminolysis can be carried out both in aqueous medium and in alcoholic ammonia solution. It is possible to use alcoholic $NH_3$ solutions (for example in MeOH, EtOH, iPrOH), but also aqueous $NH_3$ solutions (for example 25% strength).

In aqueous $NH_3$ solutions, higher $NH_3$ excesses are required; for this reason, preference is given to alcoholic $NH_3$ solutions, owing to the higher space-time yield. The process according to the invention is characterized in that the reaction can be carried out in highly concentrated form using the crude thiazolecarboxylic acid ester. If the process is carried out on an industrial scale, this results in a good space-time yield.

The conversion into the 2-aminomethyl-4-cyanothiazole (VIII) or (Ia) and (Ib) can then be carried out in a simple manner by dehydratization using, for example, trifluoroacetic anhydride, and subsequent gentle removal of the BOC protective group.

The process according to the invention is characterized in that it can be carried out in a simple manner, without costly purification. All the essential reaction steps proceed with quantitative or almost quantitative yields. The costs of the starting materials are low, and the use of toxic substances (in particular gases) can be dispensed with.

Likewise unexpected was the aminolysis of the thiazolecarboxylic acid ester with aqueous ammonia to give the thiazolecarboxamide. Preference is given to using an excess of at least 5 molar equivalents of $NH_3$, in particular of at least 10 molar equivalents of $NH_3$. It is also possible to use alcohol as solubilizer. However, in the series of the alcohols, the yields with methanol were higher than those with isopropanol. If alcohols are used, it is possible to carry out the reaction with small amounts of $NH_3$.

The thiazolecarboxylic acid ester can be obtained in crystalline form. By hydrolyzing the ester with, for example, aqueous sodium hydroxide solution, followed by pH-controlled addition of acid, it is also possible to prepare in a simple manner and with good yields the corresponding BOC-protected thiazolecarboxylic acid by this route.

For the synthesis on an industrial scale, it is advantageous to prepare the thiazolecarboxamide in a one-pot process, without isolating the ester. Starting from cysteine ester, it is thus possible to prepare the crystalline amide in a yield of >50%, at little technical expense.

The present invention relates to a process for preparing 2-aminomethyl-4-cyanothiazole and its salts of the formulae Ia and Ib

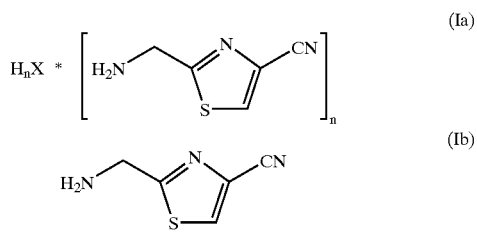

in which n=1 or 2 and for n=1, X is chloride, bromide, triflate and hydrogen sulfate and for n=2, X is sulfate, which can be obtained by introducing the tert-butyloxycarbonyl protective group (BOC) on the nitrogen of the aminoacetonitrile, followed by reaction with cysteine ester and oxidation to the corresponding thiazole-4-carboxylic acid ester and further conversion into the thiazole-4-carboxamide and finally the 4-cyanothiazole derivative.

The 4-cyanothiazoles VII and VIII are novel.

Using this process, the intermediates IV and V can be converted advantageously, without further work-up, into the respective subsequent product.

The 4-cyanothiazole salt VIII, which is embraced by the formula Ia, can be reacted under pH-controlled conditions with bases to give the salt-free form of the formula Ib.

The invention furthermore relates to processes for preparing 2-aminomethyl-4-cyanothiazole and its salts of the formulae Ia and Ib

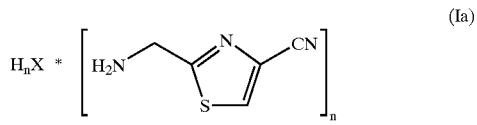

-continued

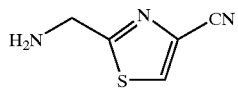
(Ib)

in which
n=1 or 2 and
for n=1, X is chloride, bromide, triflate and hydrogen sulfate and,
for n=2, X is sulfate. In the process according to the invention, the aminonitrile of the formula II

(II)

is stirred with a cysteine ester of the formula III

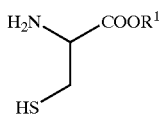
(III)

in which $R^1$ is branched or linear $C_{1-10}$-alkyl or

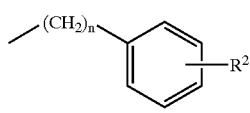

where n=0, 1 or 2 and $R^2$ is branched or straight-chain $C_1$–$C_{10}$-alkyl or $C_1$–$C_4$-alkoxy or $C_1$–$C_4$-dialkylamino, in an inert solvent in the presence of a base at from 0° C. to 80° C. until the reaction has essentially proceeded to completion.

The cysteine ester is preferably present as hydrochloride.

Moreover, according to the invention, the resulting thiazolidine IV

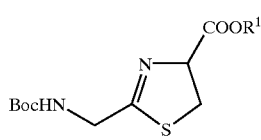
(IV)

can be oxidized in an inert solvent.
The resulting thiazolecarboxylic acid ester of the formula V

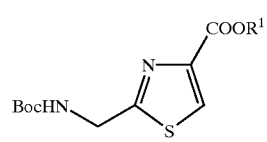
(V)

in which $R^1$ is as defined above is stirred in an alcohol $R^2OH$, in which $R^2$ is branched or linear $C_{1-8}$-alkyl, HO—$CH_2$—$CH_2$—, HO—$CH_2$—$CH_2$—$CH_2$— or $C_{1-4}$-alkyl-O—$CH_2$—$CH_2$—, at from 0° C. to 40° C. with from 1 to 50 molar equivalents of $NH_3$ until the reaction has essentially proceeded to completion.

Following the steps above, the process can be carried out without isolation of the intermediates.

The thiazolecarboxamide of the formula VI

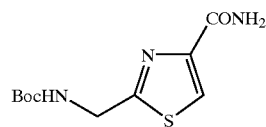
(VI)

can be filtered off as a solid.

Furthermore, the amide VI can subsequently be dehydrated to give the BOC-protected 4-cyanothiazole of the formula VII

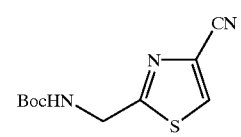
(VII)

and the BOC protective group can be removed.

Furthermore, the invention relates to a process for preparing the compound of the formula V

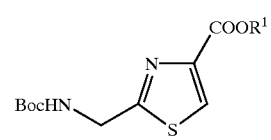
(V)

in which the aminonitrile of the formula II

(II)

is stirred with a cysteine ester of the formula III

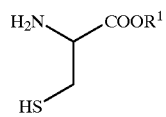
(III)

in which $R^1$ is branched or linear $C_{1-10}$-alkyl or

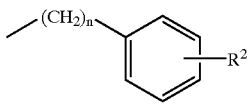

where n=0, 1 or 2 and $R^2$ is branched or straight-chain $C_1$–$C_{10}$-alkyl or $C_1$–$C_4$-alkoxy or $C_1$–$C_4$-dialkylamino in an inert solvent in the presence of a base at from 0° C. to 80° C. until the reaction has essentially proceeded to completion.

If appropriate, when preparing the compound of the formula IV

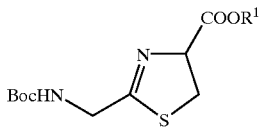

(IV)

according to the above process, the resulting thiazolecarboxylic acid ester of the formula V

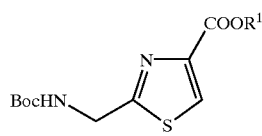

(V)

in which $R^1$ is as defined above is stirred in an alcohol $R^2OH$ at from 0° C. to 40° C. with from 1 to 50 molar equivalents of $NH_3$ in an aqueous ammonia solution until the reaction has essentially gone to completion.

Furthermore, the invention relates to compounds of the formulae Ia and Ib

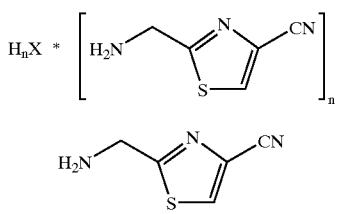

in which
n=1 or 2 and
for n=1, X is chloride, bromide, triflate and hydrogen sulfate and
for n=2, X is sulfate,
and to the compound of the formula VII

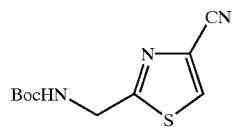

(VII)

EXAMPLE 1

Thiazolidine (IV)

205.1 g (1.31 mol) of BOC-acetonitrile are dissolved in 1160 ml of methanol and, in the presence of 23.2 g (0.23 mol) of triethylamine, admixed with 244.7 g of L-cysteine ethyl ester. The mixture is heated at 60–65° C. for 20 h. The reaction mixture is concentrated under reduced pressure and the residue is admixed with 700 ml of toluene and 300 ml of water. The mixture is stirred at room temperature for another hour. The phases are separated and the organic phase is washed twice with 200 ml of water. The combined aqueous phases are extracted with toluene. The combined organic phases are concentrated at 60° C. under reduced pressure. Yield 366.3 g (>97%)

$^1$H—NMR (DMSO—d$^6$): δ=7.4 (t, 1H, NH), 5.1 (t, 1H, CHCOOEt), 4.2 (q, 2H, OCH$_2$OCH$_3$), 3.9 (s, 2H, CH$_2$NH), 3.5 (d/d, 1 H, SCHHCH), 3.4 (d/d, 1 H, SCHHCH), 1.4 (s, 9H, tert-butyl), 1.2 (t, 3H, OCH$_2$CH$_3$) ppm.

EXAMPLE 2

Ethyl Thiazolecarboxylate (V)

464 g (1.61 mmol) of thiazolidine are dissolved in 2 l of methylene chloride and, at from −5 to 0° C., admixed with 277 g of DBU. At from −5 to 0° C., 364 g of bromotrichloromethane are then added dropwise over a period of one hour, and the mixture is stirred at this temperature for 20 h. 1 l of water is added, and the reaction mixture is allowed to warm to room temperature. The organic phase is washed with 1 l of water and 1 l of aqueous ammonium chloride solution and concentrated at 50° C. under reduced pressure.

Yield 458 g (100%), [yield corrected for purity: 96%] $^1$H-NMR (DMSO-d$^6$): δ=8.4 (s, 1H, SCHCOOEt), 7.8 (s, 1H, NH), 4.4 (d, 2H, CH$_2$NH), 4.3 (q, 2H, OCH$_2$CH$_3$, 1.4 (s, 9H, tert-butyl), 1.3 (t, 3H, OCH$_2$CH$_3$) ppm.

EXAMPLE 3

N-Ethyl-thiazolecarboxamide (VI)

33.5 g (0.18 mol) of thiazolyl ester are dissolved in 140 ml of methanol and 3 ml of water and, at 5–10° C., ammonia is introduced until the solution is saturated. The reaction mixture is stirred at room temperature overnight. The solvent is evaporated and the residue is, at 80° C., taken up in 100 ml of n-butanol. The mixture is cooled to 0° C. The precipitate is filtered off with suction, washed twice with in each case 35 ml of n-butanol and twice with in each case 35 ml of MTBE and dried under reduced pressure.

Yield 17.3 g (58%), yield corrected for purity: 55% based on the thiazolidine employed. $^1$H-NMR (DMSO-d$^6$): δ=8.2 (s, 1H, SCHCOOEt), 7.6, 7.7, 7.8 (3×s, 3×1H, 3×NH), 4.4 (s, 2H, CH$_2$NH), 1.4 (s, 9H, tert-butyl) ppm.

EXAMPLE 4

Preparation of 2-Aminomethyl-4-cyanothiazole Hydrochloride (VII)

75.0 g (0.29 mol) of BOC-protected thiazolecarboxamide (VI) were suspended in 524 ml of dichloromethane and, at from −5° to 0° C., admixed with 78.9 g (0.78 mol) of triethylamine and 79.5 g (0.38 mol) of trifluoroacetic anhydride. The mixture was stirred for one hour and allowed to warm to 20–25° C., 1190 ml of water were added and the phases were separated. 160 ml of 5-6 N isopropanolic HCl were added to the organic phase, the mixture was heated to the boil for 3 h, stirred at 20–25° C. overnight and cooled to from −5 to 0° C. for 2.5 h, and the solid was filtered off. It was washed with dichloromethane and dried. This gave 48.1 g of 2-aminomethyl-4-cyanothiazole of a purity by HPLC of 99.4 area %, which corresponds to a yield of 94.3% for these two steps.

$^1$H-NMR (DMSO-d$^6$, in ppm): 8.98 (s, broad, 2H, NH$_2$), 8.95 (s, 1H, Ar—H), 4.50 (s, 2H, CH$_2$).

EXAMPLE 5

Preparation of N-(Ethoxycarbonylmethylene)-(D)-cyclohexylalanyl-3,4-dehydroprolyl-[2-(4-hydroxyamidino)thiazole]methylamide Hydrochloride The 2-aminomethyl-4-cyanothiazole hydrochloride obtained in Example 4 is processed further as follows:

a) 3,4-Dehydroprolyl-[2-(4-cyano)thiazolylmethyl]amide Hydrochloride

2-Aminomethyl-4-cyanothiazole hydrochloride (64 g, 364 mmol) was added to a solution of BOC-3,4-dehydroproline (77.5 g, 349 mmol) in methylene chloride (150 ml). At from 0 to 10° C., diisopropylethylamine (157 g, 1.2 mol) was added dropwise with stirring to the suspension. At from −2 to −5° C., propanephosphonic acid anhydride (50% strength in ethyl acetate, 290 g, 456 mmol) was then added dropwise over a period of 2 h. After 13 h, the reaction mixture was warmed to 20° C., and 240 ml of methylene chloride and then 310 ml of water were added. The organic phase was separated off, the aqueous phase was washed with 200 ml of methylene chloride and the organic phases were combined. The collected organic phases were admixed with 200 ml of water and the pH was adjusted to pH 3 using conc. hydrochloric acid. The organic phase was separated off again and then washed with 200 ml of water. The solvent of the organic phase was distilled off and the residue was taken up in 860 ml of isopropanol. 140 ml (about 2 molar equivalents) of isopropanolic hydrochloric acid were added, and the mixture was heated to 40–45° C. After about 12 hours, the removal of the protective group was complete (TLC control). A further 140 ml of isopropanol were added, and the solution was heated at 80° C. for one hour. The mixture was subsequently slowly cooled to 0° C. and stirred at 0° C. for 18 hours, during which the title compound precipitated out as a salt. The product was filtered off and the crystals were washed with pre-cooled isopropanol and then with diisopropyl ether. 680 g (yield 72%) of the title compound were isolated as a white crystalline product.

b) N-(tert-Butoxycarbonylmethylene)-(BOC)-(D)-cyclohexylalanyl-3,4-dehydroprolyl-[2-(4-cyano)thiazole]methylamide 3,4-Dehydroprolyl-[2-(4-cyano)thiazolylmethyl]amide hydrochloride (59 g, 218 mmol) were added to a solution of N-(tert-butoxycarbonylmethylene)-(BOC)-(D)-cyclohexylalanine (preparation described in WO 9806741; 79 g, 206 mmol) in methylene chloride (640 ml). At 0–10° C., diisopropylethylamine (112 g, 867 mmol) and propanephosphonic acid anhydride solution (50% strength in ethyl acetate, 193 g, 303 mmol) were successively added dropwise. The reaction was monitored by TLC. After the reaction had proceeded to completion, the solution was warmed to room temperature, and 180 ml of water were added. The pH of the mixture was adjusted to pH 3 using conc. hydrochloric acid. The organic phase was separated off and the aqueous phase was extracted once more with 120 ml of methylene chloride. The combined organic phases were washed with a further 170 ml of water at pH 3 and then washed with 170 ml of water and dried over magnesium sulfate, and the solvent was distilled off under reduced pressure. This gave 117 g (90% yield) of the title compound as a colorless solid.

c) N-(tert-Butoxycarbonylmethylene)-(BOC)-(D)-cyclohexylalanyl-3,4-dehydroprolyl-[2-(4-hydroxyamidino)thiazole]methylamide N-(tert-butoxycarbonylmethylene)-(BOC)-(D)-cyclohexylalanyl-3,4-dehydroprolyl-[2-(4-cyano)thiazole]methylamide (22.2 g, 36.7 mmol) was dissolved in ethanol (250 ml), the solution was admixed with hydroxylamine hydrochloride (6.41 g, 92.2 mmol) and diisopropylethylamine (23.8 g, 31.6 ml, 184.5 mmol) was slowly added dropwise with cooling (water bath) to this suspension. After 3 h of stirring at room temperature, the reaction solution was concentrated under reduced pressure using a rotary evaporator, the residue was taken up in methylene chloride/water and the aqueous phase was adjusted to pH 3 using 2N hydrochloric acid and extracted. The organic phase was washed repeatedly with water, dried over magnesium sulfate and concentrated under reduced pressure using a rotary evaporator. The residue was triturated with n-hexane, giving 22.5 g of the title compound as an almost pure white solid.

d) N-Ethoxycarbonylmethylene-(D)-cyclohexylalanyl-3,4-dehydro-prolyl-[2-(4-Hydroxy-amidino)thiazole]methylamide Hydrochloride N-(tert-butoxycarbonylmethylene)-(BOC)-(D)-cyclohexylalanyl-3,4-dehydroprolyl-[2-(4-hydroxyamidino)thiazole]methylamide (2.0 g, 3.15 mmol) was dissolved in ethanol (25 ml), and the solution was admixed with 10 ml of 5N hydrochloric acid in ether and stirred at 60° C. for 3 h.

Since, according to TLC (methylene chloride/methanol/acetic acid: 100/20/5), conversion was not complete, another 10 ml of 5N hydrochloric acid in ether were added, and the mixture was stirred at 60° C. for another 3 h. The reaction mixture was concentrated under reduced pressure using a rotary evaporator and the residue was co-distilled repeatedly with ethanol and ether to remove adhering hydrochloric acid. The product was subsequently dissolved in a little methylene chloride and precipitated with ether and the residue was filtered off with suction and dried under reduced pressure. This gave 1.65 g of the title compound as a white hygroscopic solid. FAB-MS (M+H$^+$): 507

We claim:

1. A process for preparing a thiazolecarboxylic acid ester of formula V

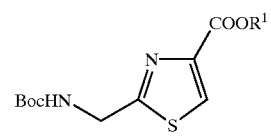

(V)

wherein $R^1$ is branched or linear $C_{1-10}$-alkyl or

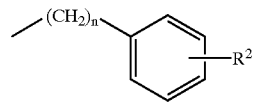

wherein n is 0, 1 or 2, and $R^2$ is branched or linear $C_{1-10}$-alkyl or $C_{1-4}$-alkoxy or $C_{1-4}$-dialkylamino, which comprises the step of preparing a thiazolidine of formula IV

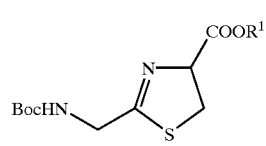

(IV)

by stirring an aminonitrile of formula II

(II)

with a cysteine ester of formula III

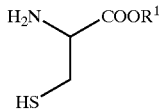
(III)

in an inert solvent in the presence of a base at from 0° C. to 80° C. until the reaction has essentially proceeded to completion.

2. A compound of the formula Ia or Ib

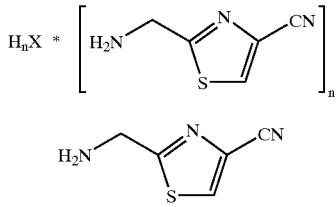
(Ia)
(Ib)

in which n=1 or 2 and for n=1, X is chloride, bromide, triflate and hydrogen sulfate and for n=2, X is sulfate.

3. A compound of the formula VII

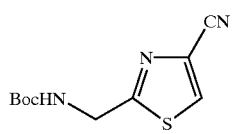
(VII)

4. The process defined in claim 1, which further comprises oxidizing the thiazolidine of formula IV in an inert solvent to obtain the thiazolecarboxylic acid ester of formula V.

5. The process defined in claim 4, wherein the preparation of the thiazolidine of formula IV and the oxidation of the thiazolidine are carried out without isolating the thiazolidine.

6. A process for preparing 2-aminomethyl-4-cyanothiazole or its salt of formulae Ia and Ib

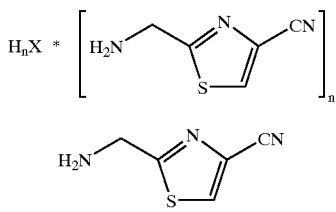
(Ia)
(Ib)

wherein n is 1 or 2, and

X is chloride, bromide, triflate or hydrogen sulfate when n is 1, and

X is sulfate when n is 2, which comprises the step of preparing a thiazolecarboxylic acid ester of formula V

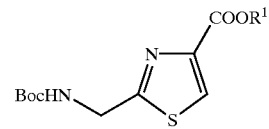
(V)

in accordance with the process defined in claim 1.

7. The process defined in claim 6, which further comprises oxidizing the thiazolidine of formula IV in an inert solvent to obtain the thiazolecarboxylic acid ester of formula V.

8. The process defined in claim 7, wherein the preparation of the thiazolidine of formula IV and the oxidation of the thiazolidine are carried out without isolating the thiazolidine.

9. The process defined in claim 7, which further comprises stirring the thiazolecarboxylic acid ester of formula V in an alcohol $R^2OH$, in which $R^2$ is branched or linear $C_{1-8}$-alkyl, $HO-CH_2-CH_2-$, $HO-CH_2-CH_2-CH_2-$ or $C_{1-4}$-alkyl-$O-CH_2-CH_2-$, at from 0° C. to 40° C. with from 1 to 50 molar equivalents of $NH_3$ until the reaction has essentially proceeded to completion, to obtain a thiazolecarboxamide of formula VI

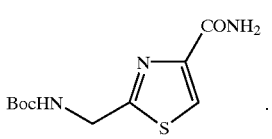
(VI)

10. The process defined in claim 9, wherein neither the thiazolidine of formula IV nor the thiazolecarboxylic acid ester of formula V are isolated for further conversion.

11. The process defined in claim 16, wherein the thiazolecarboxamide of formula VI is filtered off as a solid.

12. The process defined in claim which further comprises dehydrating the thiazolecarboxamide of formula VI to obtain a BOC-protected 4-cyanothiazole of formula VII

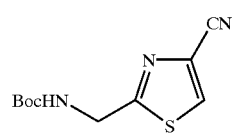
(VII)

and subsequently removing the BOC protective group from the 4-cyanothiazole of formula VII to obtain the 2-aminomethyl-4-cyanothiazole of formula Ib or its salt of formula Ia.

13. A process for preparing 2-aminomethyl-4-cyanothiazole or its salt of formulae Ia and Ib

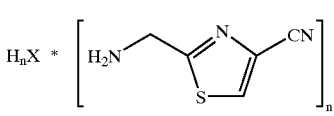
(Ia)
(Ib)

wherein n is 1 or 2, and

X is chloride, bromide, triflate or hydrogen sulfate when n is 1, and
X is sulfate when n is 2,
which comprises
stirring an aminonitrile of formula II

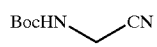
(II)

with a cysteine ester of formula III

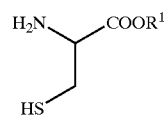
(III)

to obtain a thiazolidine of formula IV

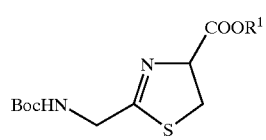
(IV)

oxidizing the thiazolidine of formula IV in an inert solvent to obtain a thiazolecarboxylic acid ester of formula V

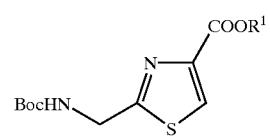
(V)

stirring the thiazolecarboxylic acid ester of formula V in an alcohol $R^2OH$, in which $R^2$ is branched or linear $C_{1-8}$-alkyl, HO—$CH_2$—$CH_2$—, HO—$CH_2$—$CH_2$—$CH_2$— or $C_{1-4}$-alkyl-O—$CH_2$—$CH_2$—, at from 0° C. to 40° C. with from 1 to 50 molar equivalents of $NH_3$ until the reaction has essentially proceeded to completion, to obtain a thiazolecarboxamide of formula VI

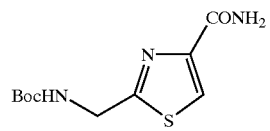
(VI)

dehydrating the thiazolecarboxamide of formula VI to obtain a BOC-protected 4-cyanothiazole of formula VII

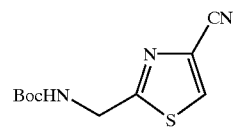
(VII)

and removing the BOC protective group from the 4-cyanothiazole of formula VII to obtain the 2-aminomethyl-4-cyanothiazole of formula Ib or its salt of formula Ia.

14. The process defined in claim 13, wherein the preparation of the thiazolidine of formula IV and the oxidation of the thiazolidine are carried out without isolating the thiazolidine.

15. The process defined in claim 13, wherein neither the thiazolidine of formula IV nor the thiazolecarboxylic acid ester of formula V are isolated for further conversion.

16. The process defined in claim 13, wherein the thiazolecarboxamide of formula VI is filtered off as a solid prior to further conversion.

* * * * *